(12) United States Patent  
Munuera Garcia (10) Patent No.: US 12,268,912 B2  
(45) Date of Patent: Apr. 8, 2025

(54) OPERATING AN ASPIRATING FIRE DETECTOR SYSTEM

(71) Applicant: Carrier Corporation, Palm Beach Gardens, FL (US)

(72) Inventor: Jose Manuel Munuera Garcia, Barcelona (ES)

(73) Assignee: CARRIER CORPORATION, Palm Beach Gardens, FL (US)

( * ) Notice: Subject to any disclaimer, the term of this patent is extended or adjusted under 35 U.S.C. 154(b) by 205 days.

(21) Appl. No.: 17/843,070

(22) Filed: Jun. 17, 2022

(65) Prior Publication Data

US 2022/0401776 A1 Dec. 22, 2022

(30) Foreign Application Priority Data

Jun. 21, 2021 (EP) .................................... 21382546

(51) Int. Cl.
  *A62C 37/50* (2006.01)
  *A62C 37/36* (2006.01)
  *G01N 1/24* (2006.01)
  *G01N 1/26* (2006.01)

(52) U.S. Cl.
  CPC .............. *A62C 37/50* (2013.01); *A62C 37/36* (2013.01); *G01N 1/24* (2013.01); *G01N 1/26* (2013.01); *G01N 2001/245* (2013.01)

(58) Field of Classification Search
  CPC ...... G01N 1/24; G01N 1/26; G01N 2001/245; A62C 37/36; A62C 37/50; G08B 17/10; G08B 29/043
  See application file for complete search history.

(56) References Cited

U.S. PATENT DOCUMENTS

| | | | |
|---|---|---|---|
| 7,015,820 B2 | 3/2006 | Bobenhausen | |
| 7,760,102 B2 | 7/2010 | Chabanis et al. | |
| 8,434,343 B2 * | 5/2013 | Rossiter ................. | G08B 17/10 |
| | | | 702/45 |
| 9,134,716 B2 | 9/2015 | Cole et al. | |
| 9,959,726 B2 * | 5/2018 | Kurtz ..................... | G08B 17/10 |

(Continued)

FOREIGN PATENT DOCUMENTS

| | | |
|---|---|---|
| CN | 105741471 A | 7/2016 |
| CN | 105960583 A | 9/2016 |

(Continued)

OTHER PUBLICATIONS

Author Unknown, "Air Sampling Smoke Detection System Titanus Top.Sens® /Rev.a", Technical Manual, Wagner Group Gmbh, Apr. 30, 2009, 213 pages.

(Continued)

*Primary Examiner* — Andre J Allen
(74) *Attorney, Agent, or Firm* — CANTOR COLBURN LLP (57) ABSTRACT

A method of operating an aspirating fire detector system (3) including a fire detector (19), a conduit (7) having an inlet and being connected to the fire detector (19), a ventilator (15) configured to draw air through the inlet of the conduit (7) and into the fire detector (19), a pressure sensor (13) configured to sense the pressure of air being that is drawn through the inlet and into the fire detector (19), and a flow meter (17) configured to measure the flow of the air drawn through the inlet and to the fire detector (19).

14 Claims, 6 Drawing Sheets

(56) References Cited

U.S. PATENT DOCUMENTS

| | | | |
|---|---|---|---|
| 10,545,041 B2 | 1/2020 | Ajay et al. | |
| 11,189,143 B2 * | 11/2021 | Ribalda Galvez ... | G08B 21/182 |
| 11,761,875 B2 * | 9/2023 | Gasparella ........... | G01K 13/024 |
| | | | 356/338 |
| 11,789,000 B2 * | 10/2023 | Maurel .............. | G01N 33/0062 |
| | | | 73/31.01 |
| 2015/0187194 A1 | 7/2015 | Hypolite et al. | |

FOREIGN PATENT DOCUMENTS

| | | | | |
|---|---|---|---|---|
| CN | 107516395 A | 12/2017 | | |
| CN | 207082201 U | 3/2018 | | |
| CN | 210743147 U | 6/2020 | | |
| CN | 111724562 A | 9/2020 | | |
| CN | 212016542 U | 11/2020 | | |
| DE | 10251891 A1 * | 4/2004 | ............. | G01F 1/696 |
| DE | 102009031099 A1 * | 12/2010 | ............. | G08B 17/10 |
| DE | 102015213385 A1 | 1/2017 | | |
| EP | 0418409 A1 | 3/1991 | | |
| EP | 0696787 A1 | 2/1996 | | |
| EP | 0772855 A1 | 5/1997 | | |
| EP | 0880766 B1 | 12/1998 | | |
| EP | 1006500 A2 * | 6/2000 | ............. | G08B 17/10 |
| EP | 1638062 A1 | 3/2006 | | |
| EP | 2393072 A1 | 12/2011 | | |
| EP | 2407946 A1 * | 1/2012 | ............. | G05B 15/02 |
| EP | 2624229 A1 | 8/2013 | | |
| EP | 4216187 A1 * | 7/2023 | ............. | A62C 37/50 |

OTHER PUBLICATIONS

European Search Report for Application No. 21382546.6; Issued Dec. 14, 2021; 15 Pages.

Schlatter Thomas: "Weather Queries: Rapid Pressure Changes near Thunderstorms, Directional Lighting", Weatherwise, vol. 40, No. 2, Apr. 1, 1987, 6 pages.

* cited by examiner

OPERATING AN ASPIRATING FIRE DETECTOR SYSTEM

FOREIGN PRIORITY

This application claims priority to European Patent Application No. 21382546.6, filed Jun. 21, 2021, and all the benefits accruing therefrom under 35 U.S.C. § 119, the contents of which in its entirety are herein incorporated by reference.

TECHNICAL FIELD OF INVENTION

The present invention relates to a method of operating an aspirating fire detector system. The invention further extends to an aspirating fire detector system and a computer programme product configured to implement the method.

BACKGROUND OF THE INVENTION

An aspirating fire detector system is a system which actively draws air from an area (or areas) to be monitored via a conduit (e.g. pipe) or network of conduits to a central fire detector, which monitors for, e.g., smoke. Aspirating fire detector systems are advantageous since they allow use of a single detector to monitor a large total area.

Aspirating fire detector systems comprise a flow meter to detect the air flow that is aspirating the detector (i.e. drawn to the detector via the conduit(s) from the area to be monitored). Changes in this air flow beyond a predetermined threshold can then be used to determine whether there has been a blockage, interruption or collapse of the conduit(s) aspirating the detector and which may result in the non-proper functioning of the aspirating fire detector system since the air from the area to be monitored cannot reach the detector as required. An alarm can then be sent to an operator indicating the non-proper functioning (i.e. a fault) of the aspirating fire detector system.

Various regulations in connection with the safe operation of aspirating fire detector systems (e.g. EN 54-20 and other certifications) require that aspirating fire detectors indicate a fault (e.g. blockage, interruption or conduit collapse) has occurred when the air flow aspirating the detector deviates by greater than ±20%. For example, if the flow measured in a normal operating condition of the aspirating fire detector system (i.e. in standby) is 5 m/s, the aspirating detector will be required to indicate a fault when the flow rate increases to 6 m/s or above, or decreases to 4 m/s or below in order for the detector system to be compliant with EN 54-20 and other regulations.

This method of fault detection however does not take account of factors which may alter the air flow but which do not result from a fault in the aspirating fire detector system (e.g. a blockage or interruption in the conduits aspirating the fire detector). For example, a change in pressure in the detected environment will alter the air flow being aspirated by the aspirated fire detector system. This is because the ventilator of the aspirating fire detector system and which draws air into the detector has more or less resistance to work against. If the pressure change is large enough in magnitude then the air flow may increase/decrease by, e.g., greater than 20%, which in turn would cause the indication of a fault despite no fault being present. Thus, without accounting for pressure changes, false fault detection in aspirating fire detector systems can occur.

Typically where it is desired to avoid false fault detection of the above type operators have modified the aspirating fire detector systems to increase the predetermined threshold of the air flow signal at which a fault is detected, e.g. in excess of 20%. Whilst this measure reduces the detection of false faults, it also reduces the likelihood of detection of actual faults and results in the aspirating fire detector system falling foul of the EN 54-20 regulation, which is not desirable.

One atypical approach to avoid false fault detection of the above-discussed type and without having to change the predetermined threshold of the air flow signal is disclosed in EP 0696787 A1. EP 0696787 A1 discloses incorporating a pressure sensor into an aspirating fire detector system. The pressure sensor detects the pressure of the air that is aspirating the detector. A detected change in air pressure is used as the basis of a correction to an air flow rate signal. The air flow rate signal, as described above, is used to determine whether there is a fault (e.g. blockage, interruption etc.) in the aspiration of the fire detector. The correction based on the change in pressure allows for false fault detections resulting from gradual pressure changes of the type discussed above to be avoided, such that false detections of blockages/interruptions in the aspirating conduits and inlets are reduced. The pressure changes disclosed in EP 0696787 A1, and upon which the correction to the flow rate signal is based upon, are, e.g., pressure changes due to changing weather and pressure changes resulting from a train ascending or descending a mountain railway.

U.S. Pat. No. 9,134,716 also discloses an aspirating fire detector system comprising both temperature and pressure sensors, and which employs a similar, atypical approach to the avoidance of false fault detections. The pressure sensor is used to detect a change in pressure in a corresponding manner to that discussed above in connection with EP 0696787 A1, whilst the temperature sensor is used to detect a change in temperature of the air/environment being monitored and which may also result in a change of air flow. In U.S. Pat. No. 9,134,716, the flow rate signal is not corrected based on a change in temperature/pressure, but rather the speed of the fan that ventilates the fire detector system is adjusted in response to the change in temperature/pressure to maintain a constant flow rate of air through the aspirating detector. This measure thereby also avoids possible false fault detection.

The prior art systems and methods described above relate to avoidance of false fault detection in aspirating fire detectors. Further improvements in this regard are desired however.

SUMMARY OF THE INVENTION

According to a first aspect of the invention, there is provided a method of operating an aspirating fire detector system comprising a fire detector, a conduit having an inlet and being connected to the fire detector, a ventilator configured to draw air through the inlet of the conduit and into the fire detector, a pressure sensor configured to sense the pressure of air that is drawn through the inlet and into the fire detector, and a flow meter configured to measure the flow of the air drawn through the inlet and to the fire detector, the method comprising: drawing air through the inlet of the conduit and to the fire detector with the ventilator; measuring the flow of the air drawn through the inlet of the conduit and to the detector using the flow meter and producing an air flow signal; measuring the pressure of the air that is drawn through the inlet of the conduit and to the detector using the pressure sensor; detecting a sudden change in pressure of the air that is drawn through the inlet of the conduit and to the detector; and implementing a corrective measure to prevent the air flow signal from exceeding or falling below a predetermined threshold as a result of the detected sudden change in pressure, wherein the predetermined threshold is indicative of a fault.

The method of the first aspect is advantageous since it allows for the avoidance of false fault detections resulting from sudden changes in pressure of the air in the environment being monitored/aspirated. The aspirating fire detector system used in the method of the first aspect of the invention will, as discussed above, be required to detect and determine faults based on the air flow signal generated by the flow meter by comparing the air flow signal to the predetermined threshold. When the air flow signal exceeds or falls below the predetermined threshold then this will indicate whether there is a fault (e.g. an interruption, blockage, collapse etc.) in the aspirating fire detector system. However, a change in air flow (and thereby a change in the flow rate signal, optionally above/below the predetermined threshold) may result from a sudden change in pressure in the environment being detected/aspirated by the aspirating fire detector system. This is because, at a given operating parameter, the ventilator of the aspirating fire detector system which draws air to the fire detector has more or less resistance to work against by virtue of the sudden pressure change. To avoid a change in air flow rate resulting from a sudden change in pressure leading to a false fault detection, the method of the first aspect detects the sudden change in pressure of the air drawn through the inlet of the conduit and to the detector and implements a corrective measure to prevent the detected sudden change from causing the air flow signal to exceed or fall below the predetermined threshold. In this way, the sudden pressure change, and resultant air flow change, is accounted for.

The majority of known aspirating fire detector systems cannot account for the effect of a pressure change of any kind, let alone a sudden pressure change, in order to avoid false fault detection. Even the unusual approaches of U.S. Pat. No. 9,134,716 and EP 0696787 A1 only allow and account for gradual pressure changes, e.g. resulting from changing weather or from a train ascending/descending a mountain railway. They are not suitable for accounting for sudden pressure changes, e.g. resulting from an ascending/descending elevator, resulting from a train entering/leaving a tunnel, resulting from an aircraft taking off or landing, resulting from an external window to a building being opened when there is a significant pressure differential between the inside of the building and the outside, etc. Thus, the method of the first aspect is advantageous over these prior art disclosures since it allows for the avoidance of false fault detections in aspirating fire detector systems resulting from sudden pressure changes in the environment/air being aspirated.

A fault may be any interruption, blockage and/or disturbance that impacts the air drawn through the inlet from reaching the fire detector.

As alluded to above, the method may further comprise comparing the air flow signal to the predetermined threshold after the corrective measure has been applied. If the air flow signal exceeds/falls below the predetermined threshold, the method may comprise issuing a signal indicating that there is a fault (e.g. a blockage, interruption or collapse of the aspirating conduit).

The predetermined threshold may be a ±20% change in the air flow signal. In this way the aspirating fire detector system can be operated in accordance with regulation EN 54-20.

The air flow signal may be a flow rate signal. The flow rate signal may be a mass flow rate signal, a volume flow rate signal or may be an air speed signal.

The corrective measure may comprise altering operating parameters of the ventilator based on the sudden change in pressure such that the air flow signal remains unaffected by the sudden change in pressure. When the sudden change in pressure is a sudden increase in pressure, the operating parameters of the ventilator may be increased such that the flow rate drawn through conduit and to the fire detector remains unchanged (i.e. to prevent the detected sudden change in pressure from affecting the air flow signal). As will be appreciated by the skilled person, a sudden increase in pressure will result in, for a given ventilator operating parameter, a lower flow of air being aspirated. As such, when a sudden increase in pressure is detected, the operating parameters of the ventilator can be increased to maintain a constant air flow and thereby a constant air flow signal. When the sudden change in pressure is a sudden decrease in pressure, the operating parameters of the ventilator may be decreased such the flow drawn through the conduit and to the fire detector remains unchanged (i.e. to prevent the detected sudden change in pressure from affecting the air flow signal).

The ventilator may be a mechanical fan. The operating parameters of the mechanical fan may comprise a rotational speed of the fan. Increasing the operational parameters of the ventilator as discussed above may comprise increasing the rotational speed of the mechanical fan. Decreasing the operational parameters of the ventilator as discussed above may comprise decreasing the rotational speed of the mechanical fan.

Implementing the corrective measure may comprise applying a correction factor to the air flow signal based on the sudden change in pressure such that the air flow signal remains unaffected by the sudden change in pressure. The correction factor may correct for the change in the air flow signal produced at the flow meter resulting from the sudden change in pressure. For instance, when there has been a sudden increase in pressure that causes the air flow through the inlet of the conduit and to the fire detector to decrease, which thereby causes the air flow signal to decrease, a correction factor may be applied to the air flow signal to raise the air flow signal back to a value as if the change in air flow resulting from the sudden pressure change had not occurred. This correction prevents the detected sudden change in pressure from affecting the air flow signal. Likewise, when there has been a sudden decrease in pressure that causes the air flow through the inlet of the conduit and to the fire detector to increase, which thereby causes the air flow signal to increase, a correction factor may be applied to the air flow signal to lower the air flow signal back to a value as if the change in air flow resulting from the sudden pressure change had not occurred.

Implementing the corrective measure may comprise altering the predetermined threshold to account for the sudden change in pressure. As above, the predetermined threshold is the value which the air flow signal may be compared with in order to determine whether there is a fault in the aspiration of the fire detector system. The alteration of the predetermined threshold to account for the sudden change in pressure may comprise altering the predetermined threshold by an amount correspondent to the amount that the air flow signal changes as a result of the sudden pressure change. For example where the air flow signal has changed by a factor of 50% as a result of the sudden change in pressure, the predetermined threshold may be altered by a factor of 50%.

The factor of 50% here is of course merely exemplary and any other factor change can equally be implemented.

In embodiments where the predetermined threshold has a magnitude (e.g. 20%) that is dependent on the magnitude of the air flow signal, the corrective measure may comprise altering the predetermined threshold such that it remains of the same relative magnitude to the air flow signal after the sudden change in pressure.

As discussed above, the sudden pressure change may be a sudden pressure increase or a sudden pressure decrease.

The sudden pressure change may be defined as a change in pressure that occurs over a suitably short time period in order to be considered as 'sudden'. As such, the sudden pressure change may be a change that occurs over a time period of 60 second or less, optionally 45 seconds, 30 seconds, 15 seconds, 10 seconds, 5 seconds or less. The sudden pressure change be a change that occurs over a time period of 1 second or less, 0.1 seconds or less, or as low as 0.01 seconds. Thus, the sudden pressure change may be change that occurs over a timescale of 0.01 seconds-60 seconds.

The sudden pressure change may be defined as a change in pressure that is large enough in magnitude in order to be considered as 'sudden'. As such, the sudden pressure change may have a magnitude of up to 10 kPa. The sudden pressure change may have a magnitude of, for instance, approximately or exactly 3.4 kPa, for example in the context of a train entering a tunnel.

The sudden pressure change may be defined as a rate of change in pressure that has a magnitude large enough in order to be considered as 'sudden'. The magnitude of the rate in change in pressure may be 1000 kPa/s or less, for instance 100 kPa/s or less, 10 kPa/s or less, 2 kPa/s or less, 1 kPa/s or less, 0.67 kPa/s or less, 0.33 kPa/s or less, 0.22 kPa/s or less, 0.17 kPa/s or less. The rate in change in pressure may be 0.057 kPa/s or less.

The pressure sensor may have response time of 60 second or less, optionally 45 seconds, 30 seconds, 15 seconds, 10 seconds, 5 seconds, 1 second or less.

The pressure sensor may be a quick response pressure sensor. As such, the pressure sensor may have response time of 0.1 seconds, 0.01 seconds, 0.001 seconds or less. Optionally the quick response pressure sensor may have a response time of 0.0005 seconds or less.

The pressure sensor may be, for example, a DMP 320 pressure sensor manufactured by SensorsONE Ltd. Such a sensor has a response time of 0.0005 seconds and can thus be considered a quick response pressure sensor.

The fire detector may be any detector suitable to detect the presence of a fire. Optionally, the fire detector is a smoke detector (i.e. a detector that detects the presence of smoke).

The pressure sensor may be situated adjacent with or within the fire detector (e.g. a component of the fire detector).

The pressure sensor may be situated in the environment being monitored by the aspirating fire detector system (i.e. the environment from which air is being aspirated from).

The pressure sensor may measure the pressure of the air as it is received at the fire detector. Additionally and/or alternatively the pressure sensor may measure the pressure of the air as it travels between the inlet of the conduit to the fire detector.

The pressure sensor may measure the pressure of the air in the environment being monitored by the aspirating fire detector system. That is, the pressure of the air might be measured upstream of the inlet of the conduit/outside of the conduit. This can be achieved with a pressure sensor located in the environment (as discussed above). Alternatively, this can be achieved by a pressure sensor situated outside the environment, but in fluid communication with the environment, for example via a capillary or similar tubing. The capillary/tubing may be distinct and separate from the conduit.

In an example, the pressure sensor may be situated adjacent to or within the fire detector and located outside of the environment being monitored, but the pressure sensor remains in fluid communication with the environment being monitored via a capillary that extends between the environment being monitored and the pressure sensor.

The aspirating fire detector system may comprise a plurality of conduits each having at least one inlet and being connected to the fire detector. One or more of the plurality of conduits may be arranged in different environments to be monitored. Alternatively and/or additionally, one or more of the plurality of conduits may be arranged in different areas of the same environment to be monitored. In this way, the aspirating fire detector system can monitor a plurality of environments and/or a larger area of the same environment.

In scenarios where the aspirating fire detector system comprises a plurality of conduits, the method may comprise drawing air through the inlets of each of the conduits and to the fire detector with the ventilator; measuring the flow of the air drawn through the inlet of each conduit and to the detector using the flow meter and producing an air flow signal; measuring the pressure of the air that is drawn through the inlet of each conduit and to the detector using the pressure sensor; detecting a sudden change in pressure of the air that is drawn through the inlet of any one of the conduits and to the detector; and implementing a corrective measure to prevent the air flow signal from exceeding or falling below a predetermined threshold as a result of the detected sudden change in pressure, wherein the predetermined threshold is indicative of a fault.

In scenarios where the aspirating fire detector system comprises a plurality of conduits, the fire detector system may optionally also comprise a plurality of flow meters and/or a plurality of pressure sensors. Each pressure sensor may measure the pressure of the air that is drawn through the inlet of one or some of the plurality of conduits to the detector. Each flow meter may measure the flow of the air drawn through the inlet of one or some of the plurality of conduits to the detector. This may result in the production of a plurality of air flow signals, one for each flow meter.

In certain embodiments, there may be a plurality of flow meters and a corresponding number of pressure sensors, one pressure sensor for each flow meter. Each flow meter may measure the flow of the air drawn through the inlet of one or some of the plurality of conduits to the detector and produce an air flow signal. Each pressure sensor may measure pressure of the air that is drawn through the inlet of the same one or some of the plurality of conduits to the fire detector. In such embodiments, the method may comprise detecting a sudden change in pressure of the air drawn through the inlet of any one of the conduits and to the fire detector; and implementing a corrective measure to prevent the air flow signal from the relevant flow meter(s) from exceeding or falling below a predetermined threshold as a result of the detected sudden change in pressure, wherein the predetermined threshold is indicative of a fault.

Alternatively, in embodiments where a plurality of conduits are provided, there may be only a single flow meter that measures the flow of the air drawn through the inlet of each of the plurality of conduits to the detector and produces an air flow signal and/or a single pressure sensor that measures the pressure of the air that is drawn through the inlet of each of the plurality of conduits to the detector.

The, or each, conduit may comprise a plurality of inlets allowing air to be drawn into the conduit at a plurality of locations. The method may thus comprise drawing air through each inlet of the conduit and to the fire detector with the ventilator.

As alluded to above, the method of operating an aspirating fire detector system of the first aspect of the invention may comprise operating an aspirating fire detector system to monitor an elevator, an elevator shaft, a train, a tunnel, an aircraft, a building or any other environment where a sudden pressure change may or is likely to occur.

The aspirating fire detector system may comprise a processor. The processor may be provided locally to one or more of: the fire detector, the ventilator, the pressure sensor, the flow meter and the conduit. Alternatively, the processor may be provided remotely from one, some or all of: the fire detector, the ventilator, the pressure sensor, the flow meter and the conduit. The processor may be in communication with one or more of: the fire detector, the ventilator, the pressure sensor, and the flow meter. The processor may carry out the method steps of detecting a sudden change in pressure of the air that is drawn through the inlet of the conduit and to the detector; and implementing a corrective measure to prevent the air flow signal from exceeding or falling below a predetermined threshold as a result of the detected sudden change in pressure, wherein the predetermined threshold is indicative of a fault.

The processor may act as a controller. The controller may control the ventilator to carry out the step of drawing air through the inlet of the conduit and to the fire detector. The processor may control the flow meter to carry out the step of measuring the flow of the air drawn through the inlet of the conduit and to the detector and to produce an air flow signal. The processor may control the pressure sensor to carry out the step of measuring the pressure of the air drawn through the inlet of the pipe and to the detector.

The processor may additionally carry out the optional step of comparing the air flow signal to the predetermined threshold after the corrective measure has been applied. The predetermined threshold may be stored in a memory in communication with the processor. If the air flow signal exceeds/falls below the predetermined threshold, the processor may further carry out a step of issuing a signal indicating that there is a fault (e.g. a blockage, interruption or collapse of the aspirating conduit).

In a second aspect of the invention there is provided a computer programme product comprising instructions that, when executed by a processor of an aspirating fire detector system, will cause the aspirating fire detector system to carry out the method of the first aspect, wherein the aspirating fire detector system comprises a fire detector, a conduit having an inlet and being connected to the fire detector, a ventilator configured to draw air through the inlet of the conduit and into the fire detector, a pressure sensor configured to sense the pressure of air that is drawn through the inlet and into the fire detector, and a flow meter configured to measure the flow of the air drawn through the inlet and to the fire detector.

The aspirating fire detector system of the second aspect may be in accordance with the aspirating fire detector system discussed above in connection with the first aspect, and may incorporate any optional feature thereof.

The computer programme product may comprise instructions that, when executed by the processor of the aspirating fire detector system, will cause the aspirating fire detector system to carry out any optional features of the method of the first aspect.

In a third aspect, there is provided an aspirating fire detector system comprising a fire detector, a conduit having an inlet and being connected to the fire detector, a ventilator configured to draw air through the inlet of the conduit and into the fire detector, a pressure sensor configured to sense the pressure of air being drawn through the inlet and into the fire detector, and a flow meter configured to measure the flow of the air drawn through the inlet and to the fire detector, wherein the fire detector system further comprises a processor that is configured to cause the aspirating fire detector system to carry out the method of the first aspect.

The aspirating fire detector system of the third aspect may be in accordance with the aspirating fire detector system discussed above in accordance with the first aspect, and may incorporate any optional features thereof.

The processor of the third aspect may be configured to carry out any optional features of the method of the first aspect of the invention.

The processor of the third aspect of the invention may comprise the computer programme product of the second aspect, and may comprise any optional features of the computer programme product of the second aspect. The computer programme product of the second aspect may thus configure the processor of the aspirating fire detector system of the third aspect to cause the aspirating fire detector system to carry out the method of the first aspect.

BRIEF DESCRIPTION OF THE DRAWINGS

Certain embodiments of the invention will now be described, by way of example only, and with reference to the accompanying drawings, in which.

DETAILED DESCRIPTION OF THE INVENTION

Figure 1:
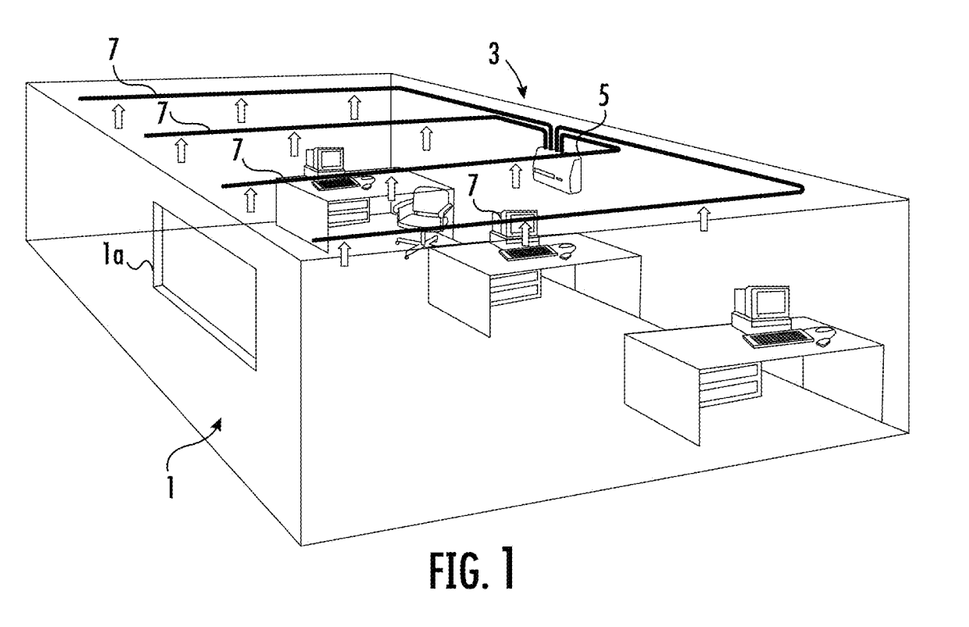
FIG. 1 depicts an aspirating fire detector system monitoring an office building.

FIG. 1 depicts an office 1 which is an environment being monitored by an aspirating fire detector system 3. The aspirating fire detector system 3 is situated within the office 1. The aspirating fire detector system 3 comprises a fire detector unit 5 positioned on a wall of the office 1, and a plurality of conduits 7 extending from the fire detector unit 5 and across the roof of the office 1. Each conduit 7 comprises a plurality of inlets positioned in the underside of the conduit. Whilst the inlets themselves are not shown in FIG. 1, the position of each of the inlets along the conduits 7 are represented by each of the upwardly pointing arrows.

Figure 2:
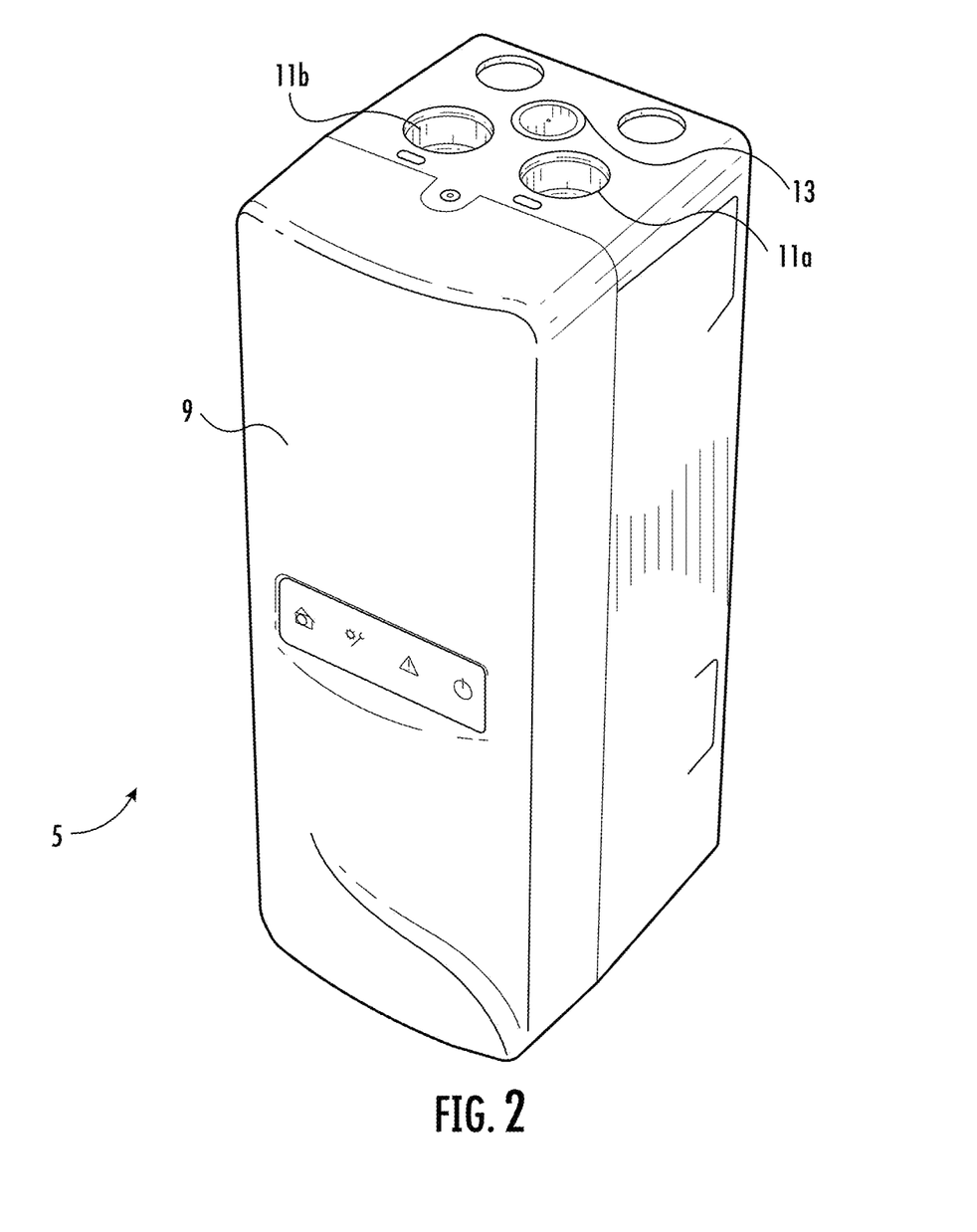
FIG. 2 depicts a fire detector unit of the aspirating fire detector system of FIG. 1.
Figure 3:
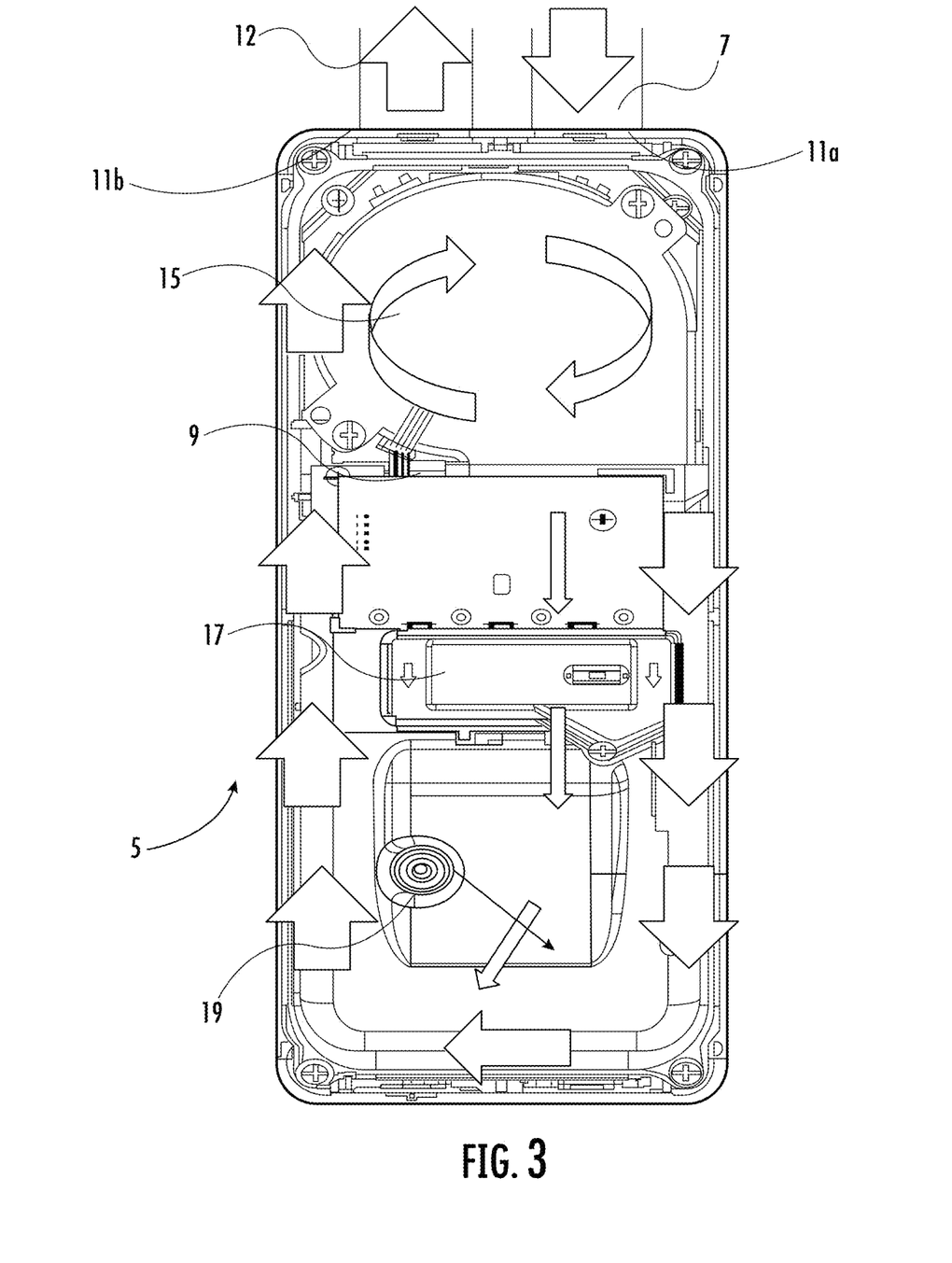
FIG. 3 is a schematic cross-sectional view of the fire detector unit of FIG. 2.

The fire detector unit 5 of FIG. 1 is depicted in FIGS. 2 and 3. The fire detector unit comprises a housing 9 with an inlet 11a and an outlet 11b extending through the housing 9.

The inlet 11a is configured to receive one of the conduits 7 into which each the other conduits 7 have joined so as to place the conduits 7 into fluid communication with an interior of the housing 9 as shown in FIG. 3. The outlet 11b is configured to receive an exhaust pipe 12 as shown in FIG. 3.

Situated on the exterior of the housing 9 is a quick response pressure sensor 13. The quick response pressure sensor 13 is a DMP 320 pressure sensor and is configured to measure the pressure in the office 1. This measurement is then used to detect whether a sudden pressure change has occurred as discussed in further detail below.

Situated within the interior of the housing 9 of the fire detector unit 5 is, as shown in FIG. 3, a ventilator in the form a mechanical fan 15, a flow meter 17 and a smoke detector 19. A processor is also comprised within the housing 9 of the fire detector unit 5, though this is not shown. The processor is in communication with the quick response pressure sensor 13, the fan 15, the flow meter 17 and the smoke detector 19.

The fan 15 is situated proximate the inlet 11a and outlet 11b is configured to rotate. Rotation of the fan 15 draws air in from the conduit 7 and through the inlet 11a into the interior of the housing 9. The action of the fan 15 causes air to circulate in the interior of the housing 9 as demonstrated by the arrows in FIG. 3, and as air is drawn in through the inlet 11a, air is simultaneously expelled from the interior of the housing 9 via the outlet 11b and through the exhaust pipe 12.

The flow meter 17 is situated beneath the fan 15 as shown in FIG. 3 and is configured to measure the air flow of the air drawn into the housing 9 by the fan 15. Specifically the flow meter 17 measures the air speed of the air drawn into the interior of the housing 9 by the fan 15 and produces an air flow signal representative of the air speed. This air flow signal is then communicated to the processor.

The smoke detector 19 is situated beneath and downstream of the flow meter 17 as shown in FIG. 3, and is configured to detect for smoke particles in the air that has passed into the interior of the housing 9 and through the flow meter 17. The smoke detector 19 is configured to communicate a signal to the processor which indicates the presence or absence of smoke in the air.

In use, the aspirating fire detector system 3 monitors for a fire in the office 1 by drawing air from the office 1 through the inlets of the conduits 7. The air is drawn into the conduits 7 from the office 1 by action of the fan 15 within the fire detector unit 5 and is drawn into the interior of the housing 9 of the fire detector unit 5 via inlet 11a. At the same time, the pressure of the air in the office 1 is measured by the quick response pressure sensor 13 and a signal indicative of the measure pressure is communicated to the processor.

A portion of the air that has been drawn into the housing 9 by the fan is passed through the flow meter 17 where the air speed is measured and an air flow signal indicative of the air speed is produced. The air flow signal is then communicated to the processor. The air flowing through the flow meter 17 is then passed through the smoke detector 19 which detects for smoke particles in the air to determine whether a fire might be present in the office. A signal indicative of whether smoke has been detected in the air is communicated from the smoke detector 19 to the processor. If the signal received by the processor indicates the presence of smoke, the processor issues an alarm signal to an operator indicating the presence of a fire in the office 1. After passing through the smoke detector 19, the air is then circulated out of the fire detector unit 5 via outlet 11b, and is exhausted back to the office 1 via the exhaust pipe 12.

The air flow signal received by the processor from the flow meter 17 is used as the basis of a determination of whether there is a fault in the aspiration of the fire detector unit 5 (e.g. a blockage, collapse or interruption of the conduits 7 used for aspirating the office 1) in. At the processor, the air flow signal is analysed to determine whether there has been a change in the air flow speed beyond a predetermined threshold of ±20%. If the air flow speed has changed by greater than ±20% then the processor determines that there is a fault in the aspiration of the fire detector unit 5 and thus issues an alarm signal to the operator indicating that there is a fault.

However, prior to the air flow signal being analysed by the processor to determine whether there has been a ±20% change in the air flow speed, the processor analyses the signal received from the quick response pressure sensor 13 to detect whether there has been a sudden change in pressure of the air drawn through the inlets of the conduits 7 and to the fire detector unit 5. For instance, the processor analyses the signal received from the quick response pressure sensor 13 to detect whether there has been a sudden change in pressure resulting from external window 1a being opened in the office 1.

The processor determines whether there has been a sudden change in pressure if the signal from the pressure sensor shows a change in pressure of greater than or equal to 0.057 kPa/s. If a sudden change in pressure is detected, then the processor acts to implement a corrective measure to prevent the air flow signal from exceeding or falling below the predetermined threshold of ±20% as a result of the detected sudden change in pressure.

In the embodiment of FIG. 1, two corrective measures may be implemented by the processor in response to a sudden pressure change. In a first alternative, the processor may control the fan 15 to alter its rotational speed in order to alter the speed of the air that is drawn into the fire detector unit 5. In that way, the processor can correct for the change in air speed, and thus the change in the air flow signal, that results from the sudden pressure change by altering the performance of the fan 15. As such, the air speed and thus the air flow signal remains unaffected by the sudden change in pressure.

In a second alternative, the processor does not alter the rotational speed of the fan 15, but instead applies a correction factor to the air flow signal produced at the flow meter 17 based on the sudden change in pressure. The magnitude of the correction factor to be applied to the air flow signal is dependent on the magnitude of the sudden pressure change. The correction factor corrects for the change in the air flow signal that has resulted from the sudden change in pressure, and in that way the sudden change in pressure does not affect the air flow signal to be analysed by the processor in order to detect for the presence of a fault.

By detecting whether a sudden pressure change has occurred prior to analysing the air flow signal and implementing a corrective measure, false fault detections (e.g. a false detection of a blockage or interruption of the conduits 7) of the aspiration of the fire detector system 3 can be avoided.

As will be clear from the above discussion, the modality used in the aspirating fire detector system 3 to determine whether there has been a fault relies on an air flow signal which is indicative of air flow received by the fire detector unit 9. However, as will also be clear from the foregoing discussion and as will be apparent to skilled person, a sudden pressure change can alter the air flow received by the fire detector unit 5 which in turn has the potential to cause a detection of a fault despite no fault occurring.

The operation of the aspirating fire detection system 3 as discussed above however avoids false fault detections of the above type because a corrective measure is applied in light of the sudden pressure change such that the air flow signal does not exceed or fall below the predetermined threshold that is indicative of a fault as a result of the sudden change in pressure. Thus, when the air flow signal is analysed subsequent to the corrective measure being implemented to determine the presence of a fault, it is not affected by the sudden pressure change. Thus, the aspirating fire detection system 3 and method of operation of the aspirating fire detector system 3 provide improved reliability since false faults resulting from sudden pressure changes, which would be detected by prior art systems, are avoided.

Figure 4:
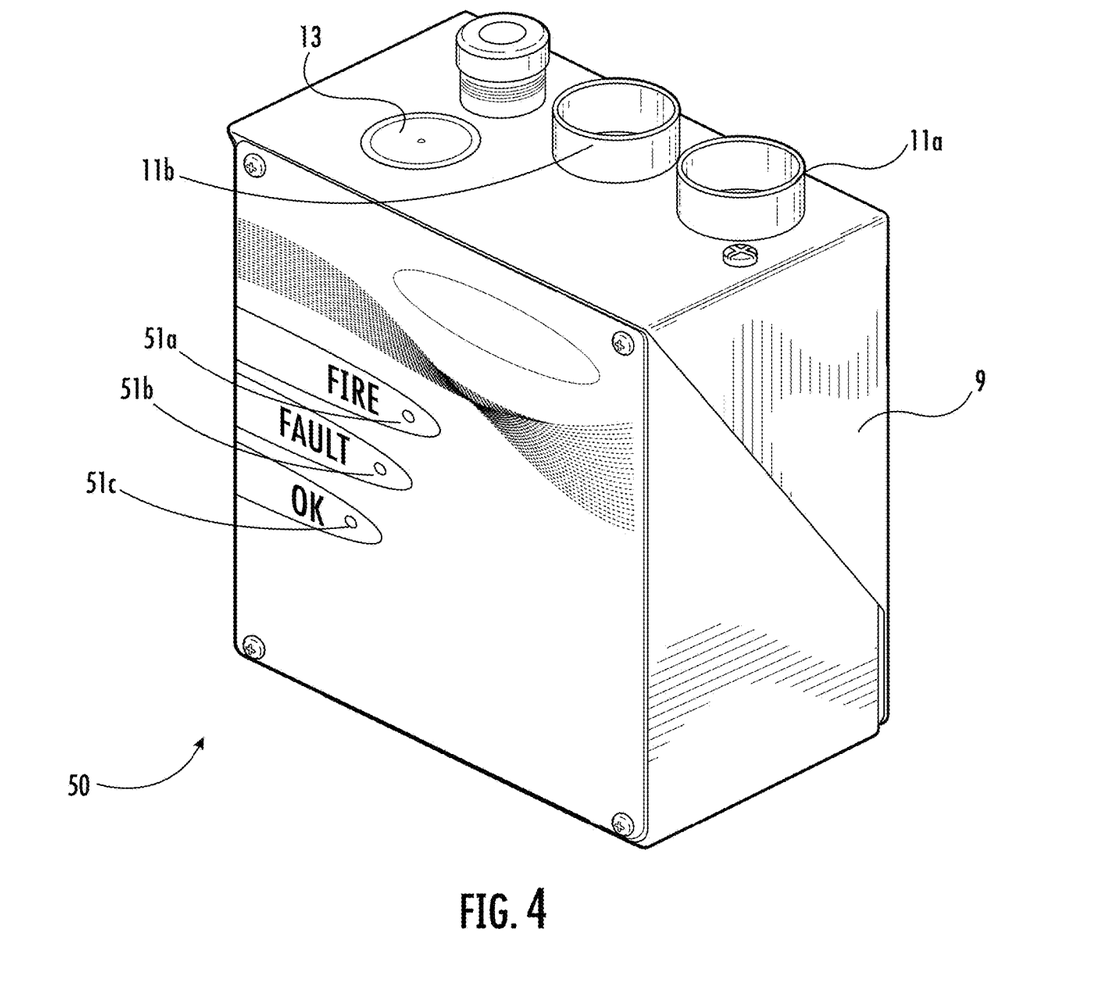
FIG. 4 depicts an alternative fire detector unit for use in an aspirating fire detector system.

FIG. 4 shows an alternative embodiment of a fire detector unit 50. The construction and functionality of the fire detector 50 is broadly similar to that of the fire detector 5 of FIGS. 2 and 3. For instance, as shown in FIG. 4, the fire detector 50 comprises a housing 9 with an inlet 11*a* and an outlet 11*b* extending through the housing 9. The inlet 11*a* is configured to receive a conduit 7 so as to place the conduit 7 into fluid communication with an interior of the housing 9. The outlet 11*b* is configured to receive an exhaust pipe 12. Similarly, situated on the exterior of the housing 9 of the fire detector 50 is a quick response pressure sensor 13.

The housing 9 of fire detector 50 comprises three LED lights 51*a*, 51*b* and 51*c*. These LEDs 51*a*, 51*b* and 51*c* are in communication with the processor within the fire detector unit 50. LED 51*a* is configured to emit light in response to an alarm signal from the processor indicating the presence of a fire. LED 51*b* is configured to emit light in response to a signal from the processor indicating the presence of a fault in the aspiration of the fire detector. LED 51*c* is configured to emit light when neither of the fault or alarm signals is received from the processor to indicate an 'OK' situation of the aspirating fire detector system 3. LED 51*c* thus acts as an indication that the aspirating fire detection system 3 is operational when an alarm or fault signal is not being indicated by LEDs 51*a* and 51*b*.

Figure 5:
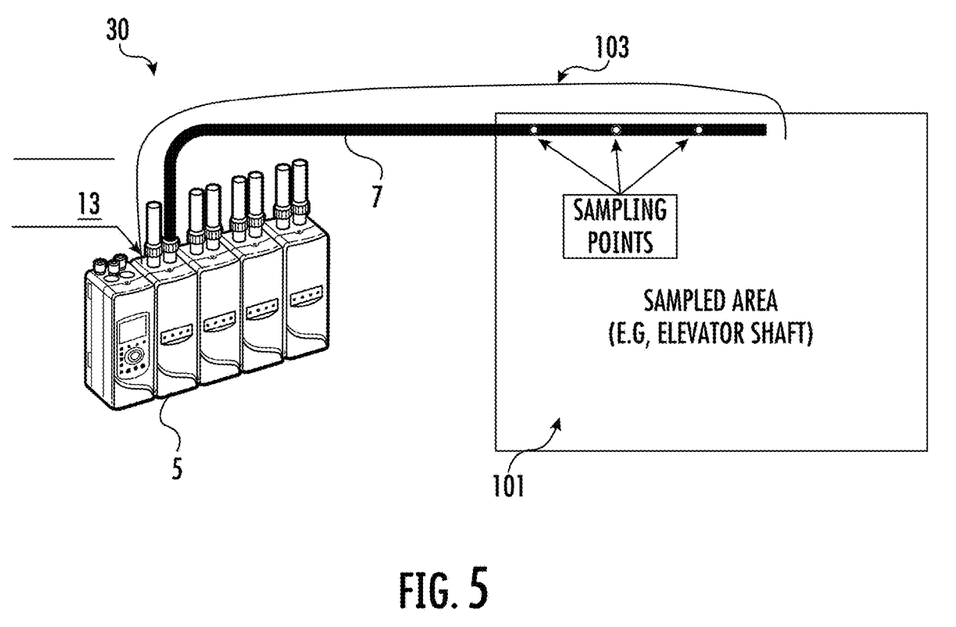
FIG. 5 depicts an aspirating fire detector system monitoring an elevator shaft.

FIG. 5 shows an alternative embodiment of an aspirating fire detector system 30 that is operating to monitor a different environment. Specifically, the aspirating fire detector system 30 is monitoring an elevator shaft 101.

The features, operation and functionality of the aspirating fire detector system 30 as depicted in FIG. 5 are largely correspondent to that of the fire detector system 1. In particular, the fire detector system 30 has the ability to avoid false fault detection that may arise from a sudden pressure from, e.g., an ascending and descending elevator in the elevator shaft 101.

Where the aspirating fire detector system 30 differs from the fire detector system 3 however is that the fire detector unit 5 is not situated in the environment being monitored (i.e. in the elevator shaft 101). To ensure therefore that the pressure sensor 17 of the aspirating fire detector system 30 can detect sudden pressure changes occurring in the elevator shaft 101, a capillary 103 is provided between the interior of the elevator shaft 101 and the pressure sensor 13. In that way, the pressure sensor 101 is in fluid communication with the elevator shaft 101 and can hence measure the pressure therein and thereby be used to detect sudden pressure changes in the elevator shaft 101.

Figure 6:
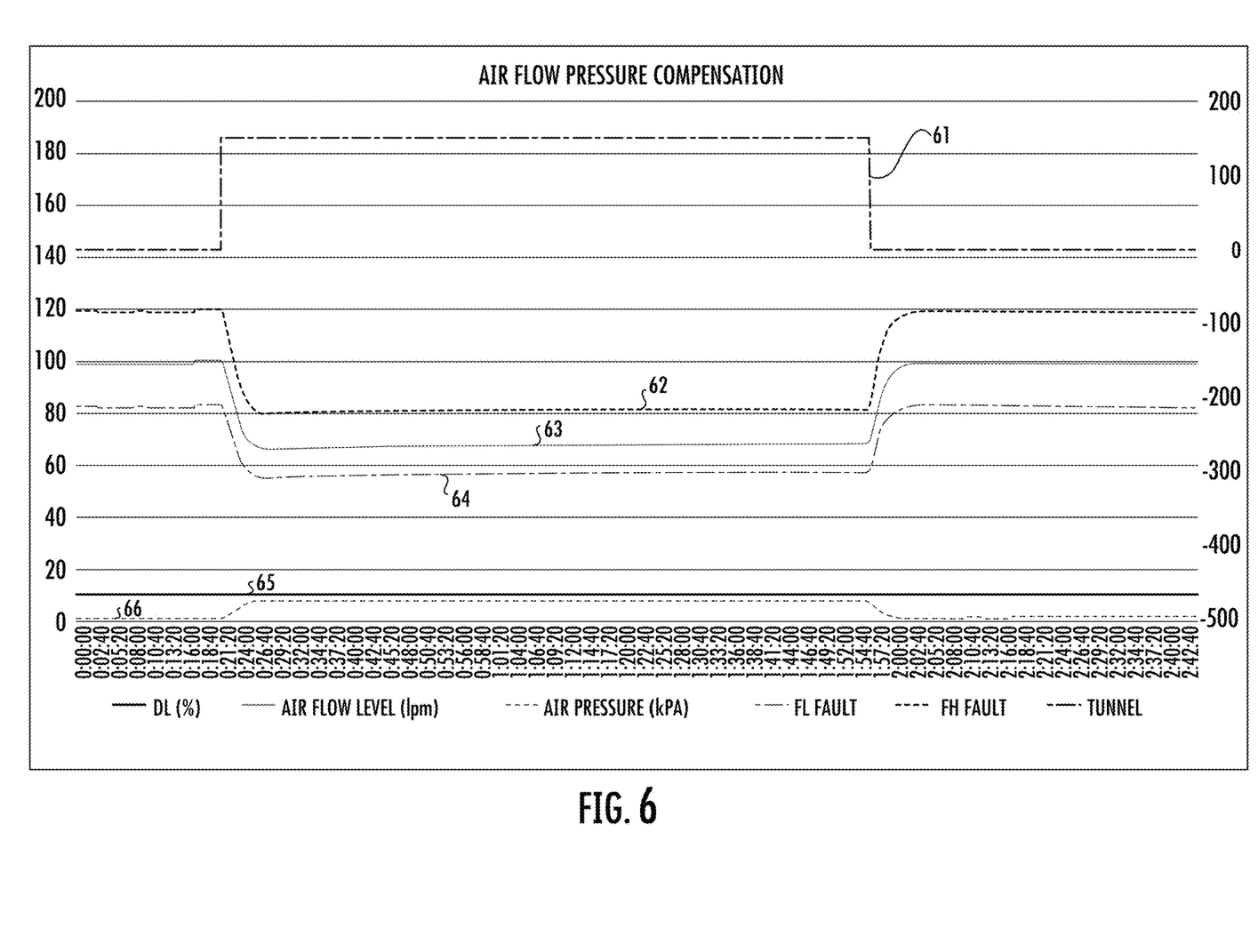
FIG. 6 is a graphical representation of an air flow signal produced by an air flow meter of an aspirating fire detector system, and a corrective measure which is implemented in view of a sudden pressure change.

FIG. 6 is a graphical representation of an air flow signal produced by an air flow meter 17 of an aspirating fire detector system, and a corrective measure which is implemented in view of a sudden pressure change. Specifically, FIG. 6 represents the air flow signal produced by an aspirating fire detector system monitoring a train as it passes through a tunnel. Line 61 represents the passage of the train through the tunnel and is used for figurative purposes only. The period of increase in line 61 is representative of the time that the trains spends in the tunnel.

Line 63 represents the raw, uncorrected air flow signal (in units of litres per minute) produced by the air flow signal and line 66 represents the detected air pressure (in units of kPa). As can be seen in FIG. 6, at approximately 0:21:20 there is a sudden drop in the air flow signal 63 that lasts until approximately 2:00:00, at which point the air flow signal 63 returns suddenly back to approximately its initial value. This is caused by the passage of the train through the tunnel as shown in line 61.

Correspondingly, as also shown in FIG. 6, there is a sudden increase in the air pressure detected by the pressure sensor 66 at approximately 0:21:20 that lasts until approximately 2:00:00 as result of the train entering the tunnel. The sudden drop and subsequent sudden rise in the air flow signal 63 results from the sudden increase and subsequent sudden decrease in the air pressure 66 resulting from the train entering and leaving the tunnel. As can be seen in FIG. 6, the sudden decrease in pressure causes a decrease in the air flow signal 63 of approximately 30%. As discussed above, for an aspirating fire detector system to be, e.g., compliant with the EN 54-20 regulations, the aspirating fire detector system is required to issue a fault warning when there is a change of greater than ±20% in the flow rate signal. As demonstrated in FIG. 6 however, a sudden change in pressure can result in a change in the flow rate signal of greater than ±20%. As such, without implementing a corrective measure to account for a sudden change in pressure the aspirating fire detector system would issue a fault warning despite no fault being present.

Lines 62 and 64 represent the pre-determined threshold of the aspirating fire detector 3, 103. Initially lines 62 and 64 have a value of 120 litres per minute and 80 litres per minute respectively, and thus represent ±20% of the initial air flow signal 63, itself having a value of 100 litres per minute initially. Should the air flow signal 63 exceed line 62 or fall below line 64 then a fault would be indicated by the aspirating fire detector 3, 103.

At approximately 0:21:20, i.e. the point where there is a sudden pressure increase in the pressure 61 and also where the air flow signal 63 decreases as a result of the sudden pressure increase, it can be seen that the predetermined threshold lines 62 and 64 also decrease. This decrease in the predetermined threshold 62, 64 results from a corrective measure implemented in light of the sudden pressure change that is detected. As will be appreciated from FIG. 6 and the discussion above, if the predetermined thresholds 62, 64 were not altered in response to the sudden pressure change then the air flow signal 63 would fall below the threshold 64 and a fault would be falsely indicated by the aspirating fire detector system. Therefore, to avoid this false fault detection and in response to the sudden change in pressure that is detected, threshold 62, 64 is altered relative to the new pressure that is detected such that they remain at ±20% of the air flow signal. This corrective measure prevents the detected sudden change in pressure from causing the air flow signal 63 to exceed or fall below the threshold 62, 64 that would cause a false fault detection.

At approximately 2:00:00, i.e. the point where there is a sudden pressure decrease in the pressure detected at the pressure sensor 66 and also where the air flow signal 63 increase as a result of the sudden pressure decrease, it can be seen that the predetermined threshold lines 62 and 64 increase. This increase is a result of another corrective measure implemented in light of the detected sudden pressure change, and ensures that the thresholds 62, 64 remain at ±20% of the air flow signal, thus maintaining EN 54-20 compliance, irrespective of any sudden pressure changes.

What is claimed is:

1. A method of operating an aspirating fire detector system (3, 30) comprising a fire detector (19), a conduit (7) having an inlet and being connected to the fire detector (19), a ventilator (15) configured to draw air through the inlet of the conduit (7) and into the fire detector (19), a pressure sensor (13) configured to sense the pressure of air that is drawn through the inlet and into the fire detector (19), and a flow meter (17) configured to measure the flow of the air drawn through the inlet and to the fire detector (19), the method comprising:

drawing air through the inlet of the conduit (7) and to the fire detector (19) with the ventilator (15);

measuring the flow of the air drawn through the inlet of the conduit (7) and to the detector (19) using the flow meter (17) and producing an air flow signal;

measuring the pressure of the air that is drawn through the inlet of the conduit (7) and to the fire detector using the pressure sensor (13);

detecting a sudden change in pressure of the air that is drawn through the inlet of the conduit (7) and to the fire detector (19); and implementing a corrective measure to prevent the air flow signal from exceeding or falling below a predetermined threshold as a result of the detected sudden change in pressure, wherein the predetermined threshold is indicative of a fault.

2. A method as claimed in claim 1, comprising comparing the air flow signal to the predetermined threshold after the corrective measure has been applied, and if the air flow signal exceeds or falls below the predetermined threshold, the method comprises issuing a signal indicating that there is a fault.

3. A method as claimed in claim 1, wherein the predetermined threshold is a 20% change in the air flow signal.

4. A method as claimed in claim 1, wherein the corrective measure comprises altering operating parameters of the ventilator (15) based on the sudden change in pressure such that the air flow signal remains unaffected by the sudden change in pressure.

5. A method as claimed in claim 4, wherein the ventilator is a mechanical fan (15), and wherein altering the operating parameters comprises altering the rotational speed of the mechanical fan (15).

6. A method as claimed in claim 1, wherein implementing the corrective measure comprises applying a correction factor to the air flow signal based on the sudden change in pressure such that the air flow signal remains unaffected by the sudden change in pressure.

7. A method as claimed in claim 1, wherein implementing the corrective measure comprises altering the predetermined threshold to account for the sudden change in pressure.

8. A method as claimed in claim 1, wherein the sudden pressure change is a change that occurs over a time period of 60 second or less, optionally 45 seconds, 30 seconds, 15 seconds, 10 seconds, 5 seconds or less.

9. A method as claimed in claim 1, wherein the sudden pressure has a magnitude of up to 10 kPa.

10. A method as claimed in claim 1, wherein the sudden pressure change has a rate in change in pressure of magnitude of 1000 kPa/s or less, 100 kPa/s or less, 10 kPa/s or less, 2 kPa/s or less, 1 kPa/s or less, 0.67 kPa/s or less, 0.33 kPa/s or less, 0.22 kPa/s or less, 0.17 kPa/s or less, or 0.057 kPa/s or less.

11. A method as claimed in claim 1, wherein the pressure sensor (13) is situated outside of an environment (101) being monitored by the aspirating fire detector system (30), and wherein the aspirating fire detector system (30) comprises a capillary (103) providing fluid communication between the pressure sensor (13) and the environment (101) being monitored by the aspirating fire detector system (30).

12. A method as claimed in claim 1, wherein the aspirating fire detector system (3) comprises a plurality of conduits (3) that each have an inlet, and wherein the method comprises drawing air through the inlets of each of the conduits (7) and to the fire detector (19) with the ventilator (15); measuring the flow of the air drawn through the inlet of each conduit (7) and to the fire detector (19) using the flow meter (17) and producing an air flow signal; measuring the pressure of the air that is drawn through the inlet of each conduit (7) and to the fire detector using the pressure sensor (13); detecting a sudden change in pressure of the air that is drawn through the inlet of each conduit (7) and to the fire detector (19); and implementing a corrective measure to prevent the detected sudden change in pressure from affecting the air flow signal.

13. A computer programme product comprising instructions that, when executed by a processor of an aspirating fire detector system (3, 30), will cause the aspirating fire detector system (3, 30) to carry out the method of claim 1, wherein the aspirating fire detector system (3, 30) comprises a fire detector (19), a conduit (7) having an inlet and being connected to the fire detector (19), a ventilator (15) configured to draw air through the inlet of the conduit (7) and into the fire detector (19), a pressure sensor (13) configured to sense the pressure of air to be drawn through the inlet and into the fire detector (19), and a flow meter (17) configured to measure the flow of the air drawn through the inlet and to the fire detector (19).

14. An aspirating fire detector system (3, 30) comprising a fire detector (19), a conduit (7) having an inlet and being connected to the fire detector (19), a ventilator (15) configured to draw air through the inlet of the conduit and into the fire detector (19), a pressure sensor (13) configured to sense the pressure of air to be drawn through the inlet and into the fire detector (19), and a flow meter (17) configured to measure the flow of the air drawn through the inlet and to the fire detector (19), wherein the aspirating fire detector system (3, 30) further comprises a processor configured to carry out the method of claim 1.

* * * * *